United States Patent
Sharon (10) Patent No.: US 7,101,365 B1
(45) Date of Patent: Sep. 5, 2006

(54) LASER FOR SKIN TREATMENT

(75) Inventor: Uzi Sharon, Tel-Aviv (IL)

(73) Assignee: I.T.L. Optronics, Ltd., Petach-Tikva (IL)

( * ) Notice: Subject to any disclaimer, the term of this patent is extended or adjusted under 35 U.S.C. 154(b) by 0 days.

(21) Appl. No.: 09/744,445

(22) PCT Filed: May 25, 1999

(86) PCT No.: PCT/IL99/00279

§ 371 (c)(1),
(2), (4) Date: Jan. 22, 2001

(87) PCT Pub. No.: WO00/71045

PCT Pub. Date: Nov. 30, 2000

(51) Int. Cl.
A61B 18/18 (2006.01)
A61B 18/20 (2006.01)
A61N 5/067 (2006.01)

(52) U.S. Cl. .............................. 606/9; 606/10; 606/12; 607/88; 607/89

(58) Field of Classification Search .............. 606/8–13, 606/16–18; 607/88–91; 128/898
See application file for complete search history.

(56) References Cited

U.S. PATENT DOCUMENTS

| 4,686,992 | A | | 8/1987 | Dewey et al. |
| 5,049,147 | A | | 9/1991 | Danon |
| 5,437,290 | A | * | 8/1995 | Bolger et al. .............. 128/898 |
| 5,531,740 | A | | 7/1996 | Black |
| 5,628,744 | A | | 5/1997 | Coleman et al. |
| 5,653,706 | A | * | 8/1997 | Zavislan et al. .............. 606/9 |
| 5,823,993 | A | * | 10/1998 | Lemelson .................... 604/51 |
| 5,865,829 | A | * | 2/1999 | Kitajima ....................... 606/3 |

FOREIGN PATENT DOCUMENTS

| DE | 3837248 | 5/1990 |
| EP | 0 880 941 | 12/1998 |
| WO | WO 99/11324 | 3/1999 |

OTHER PUBLICATIONS

Welch, A. J. et al.; "Introduction to Medical Applications"; Optical-Thermal Response of Laser-Irradiated Tissue; pp. 609-618; 1995.
Finkel, B. et al.; "Pulsed Alexandrite Laser Technology for Noninvasive Hair Removal"; Journal of Clinical Laser Medicine & Surgery; vol. 15; No. 5; pp. 225-229; 1997.
Grossman, M.C. et al.; "Damage to Hair Follicles by Normal-Mode Ruby Laser Pulses"; Journal of the American Academy of Dermatology; pp. 889-894; Dec. 1996.
Van Gemert, M. J. C. et al.; "Laser Treatment of Port Wine Stains"; Optical-Thermal Response of Laser-Irradiated Tissue; pp. 789-829; 1995.

* cited by examiner

Primary Examiner—A. Farah
(74) Attorney, Agent, or Firm—Fenster & Company (57) ABSTRACT

A laser system for treating features on the skin of a patient with laser light comprising: an imaging subsystem that locates features on the skin to be treated; a laser; laser optics that focuses light from the laser onto a feature located by the imaging subsystem; and a controller that when a feature is located, controls the laser to radiate a pulse of laser light that is focused by the laser optics to a spot localized about the feature.

37 Claims, 5 Drawing Sheets

LASER FOR SKIN TREATMENT

RELATED APPLICATIONS

The present application is a US National application of PCT/IL99/00279, filed 25 May 1999.

FIELD OF THE INVENTION

The invention relates to laser devices and especially to laser devices used for cosmetic and surgical treatment of the skin.

BACKGROUND OF THE INVENTION

The use of lasers in corrective and cosmetic surgery procedures is well known. In these procedures light from a laser comprised in an appropriate mechanical-optical system causes a desired cosmetic or surgical change in a region of tissue by delivering to the region an amount of energy sufficient to effect the change. A common problem often encountered in these procedures is to deliver the energy to the region, hereinafter referred to as a "target", without delivering energy to tissue surrounding the region that might damage the surrounding tissue. Many prior art medical laser systems do not solve this problem satisfactorily and often deliver substantial amounts of unwanted and unneeded energy to tissue surrounding a target that they irradiate.

For example, laser light is often used to depilate skin by cauterizing follicles of hair to be removed from the skin. Most prior art laser depilators irradiate areas of skin much larger than the area of skin occupied by a hair follicle. As a result, most of the laser energy these depilators radiate is wasted. A major portion of the laser energy is incident on hairless areas of skin and only a small portion is incident on targets (i.e. hair follicles) on the skin and used to remove hair. Since the prior art laser depilators are energy inefficient, they generally require relatively powerful lasers that illuminate skin being treated with a high energy density of laser light. This energy density when incident on hairless regions of skin can cause thermal damage to these areas.

For example, typically 20 milliJoules (mJ) of energy are required to cauterize a hair follicle and a typical hair follicle occupies an area of skin approximately $3 \times 10^{-4}$ cm$^2$. An energy density of about 60 J/cm$^2$ therefore is generally required to cauterize hair follicles. Many prior art laser depilators irradiate an area of skin on the order of 1 cm$^2$ with a pulse of laser energy lasting about a millisecond or a fraction of a millisecond to depilate an area of skin. A Laser in one of these systems must therefore provide a peak power output of about 60,000 watts.

SUMMARY OF THE INVENTION

An aspect of some preferred embodiments of the present invention relates to providing a laser system for medical/cosmetic treatment of skin, such as for hair removal, coagulation of varicose veins and the removal of skin tumors, that minimizes the amount of laser energy incident on tissue surrounding targets that the system irradiates.

According to an aspect of some preferred embodiments of the present invention, the laser system comprises an optical imaging subsystem that scans the skin of a patient being treated and identifies and locates targets for treatment in the area.

Preferably, the optical imaging subsystem comprises a microscope that collects light from an object that it images and focuses the collected light to form a magnified image of the object on a photosensitive surface. The skin being treated is optically scanned by positioning the microscope's objective lens close to the skin and moving the microscope so as to image different regions of the skin onto the photosensitive surface. Image data from the photosensitive surface characteristic of an imaged region are transmitted to circuitry that analyzes the data to determine if a target is located in the imaged region. Preferably, an imaged region is determined to have a target if a portion of the image exhibits characteristics typical of a target and the portion corresponds to an area of the skin substantially centered at the focal point of the microscope.

Preferably, the laser system comprises a light source that illuminates regions of the skin imaged by the microscope with light having a spectrum that enhances the contrast between targets and clear skin devoid of targets.

For example, assume that the skin is being depilated, that targets on the skin to be searched for are hair follicles and that the skin is illuminated with light for which hair follicles have relatively low reflectance compared to the reflectance of clear skin. Since the hair follicles are expected to reflect less light than clear skin, the imaging subsystem will search for relatively dark areas on the skin having a size characteristic of hair follicles. If such a relatively dark area is found in an imaged region of the skin and the dark area is substantially centered at the focal point of the microscope, the imaged region is determined to have a target for irradiation.

According to an aspect of some preferred embodiments of the present invention the laser system comprises a laser and associated optical elements that are controllable to irradiate with laser energy substantially only targets identified by the imaging subsystem.

The optical elements preferably focus light from the laser to a spot centered at the focal point of the microscope. The spot size is preferably determined with reference to the sizes of targets to be treated with the system. Preferably, the spot size is determined to be a small multiple of an expected characteristic size of the targets. In some preferred embodiments of the present invention it is less than three times the size of the feature. Preferably, the spot size is smaller than twice the characteristic size of the feature. More preferably the spot size is less than 1.5 times the characteristic size of the feature. Most preferably, the spot size is greater than about 1.2 times the characteristic size of the feature. For example, if the laser system is being used to depilate skin, the spot size is preferably determined to be a small multiple of a characteristic size of a hair follicle. A characteristic size of a hair follicle might be an average size of a hair follicle or a hair follicle size that is greater than the size of 95% of the hair follicles. If the laser unit is being used to eradicate small tumors, a characteristic size is a suitable expected size of the tumors.

The laser is preferably turned on and off by a controller. During the scan of a treated area of skin the laser is normally off. However, when an imaged region of the skin is determined to have a target located within a "spot size" of the microscope's focal point, the controller turns the laser on to deliver a pulse of laser light to a spot centered at the focal point and thereby to the target. Preferably, the controller determines the energy in the pulse by controlling the pulse width and/or the intensity of light in the light pulse.

The scan speed of the imaging subsystem is preferably sufficiently slow so that the imaging system remains focused substantially on a same region of skin during the time it takes to determine whether an imaged region has a target and energize the laser. Furthermore, as noted above, the spot size to which a light pulse is focused, is preferably slightly larger than a target defined by a feature of the skin that is to be irradiated. Therefore, the energy in laser light pulses radiated by the laser system is substantially restricted to areas of targets or areas immediately surrounding targets. For example the energy in a laser light pulse might be restricted to an area having a diameter 1.5 or 2 times the diameter of the area of a target that the light pulse irradiates.

Thus, with a laser system in accordance with a preferred embodiment of the present invention, laser energy used to effect cosmetic or surgical changes in the skin of a patient is substantially restricted to only those areas of the skin that require treatment. Little of the energy radiated by the system is incident on skin areas where it is not needed.

A laser system in accordance with a preferred embodiment of the present invention therefore uses laser energy efficiently and can generally treat features on a patient's skin using a laser having substantially lower power output than lasers used in comparative prior art systems. For example in a laser depilator, in accordance with a preferred embodiment of the present invention, laser energy is focused to a spot size of about $3 \times 10^{-4}$ cm$^2$. Laser energy is delivered to cauterize a hair follicle in a laser pulse having a pulse width of about 2 milliseconds. Assuming 20 mJ of energy is needed to cauterize the hair follicle a laser that provides the pulse has to supply a peak power of about 10 watts. The laser depilator, in accordance with a preferred embodiment of the present invention, uses a laser having a peak power output about one thousandth that used in many prior art laser depilators.

Whereas in the example given above a laser providing a peak power of ten watts is used, a laser that provides different peak power output is useable in a laser system in accordance with a preferred embodiment of the present invention. Preferably the peak power of the laser is less than 100 watts. More preferably the peak power is less than 50 watts. Most preferably the peak power is less than 30 watts.

According to an aspect of some preferred embodiments of the present invention the microscope, photosensitive surface and laser are mounted in a hand unit. To treat a patient an operator of the laser system holds the hand unit with the microscope objective lens close to and facing the patient's skin. The operator moves the hand unit substantially parallel to the skin to scan an area of the skin for targets. As targets are identified, they are irradiated with laser light from the laser.

In accordance with an aspect of some preferred embodiments of the present invention the microscope is preferably mounted in the hand unit so that it is rotatable about an axis of rotation that is perpendicular to the microscope's optic axis and fixed with respect to the hand unit. The microscope is coupled to a motor or actuator in the hand unit that rotates the microscope about the axis back and forth through a predetermined angle. The focal point of the microscope therefore moves back and forth, near to or on the surface of the patient's skin, along a direction perpendicular to the axis of rotation of the microscope. The operator preferably moves the hand unit along the skin in a direction substantially parallel to the axis of rotation. As a result of the back and forth motion of the focal point of the microscope and the motion of the hand unit, the imaging system scans a ribbon shaped area on the patient's skin and target regions in the area are identified and irradiated. There is thus provided, in accordance with a preferred embodiment of the invention, a laser system for treating features on the skin of a patient with laser light comprising:

an imaging subsystem that locates features on the skin to be treated;

a laser;

laser optics that focuses light from the laser onto a feature located by the imaging subsystem; and a controller, that when a feature is located, controls the laser to radiate a pulse of laser light that is focused by the laser optics to a spot localized about the feature.

Preferably, the system includes a light source that illuminates regions imaged by the imaging optics with light for which the features to be treated have a reflectance different from that of clear skin so that a feature to be treated appears as a contrasted sub-region of an imaged region of the skin.

Preferably, the spectrum of the light radiated by the light source is tunable.

Preferably, the spot to which the laser is focused has an area substantially equal to an area characteristic of the size distribution of areas occupied on the skin by features to be treated, multiplied by a factor greater than one. Preferably, the factor is less than 2 or 1.5.

Preferably, the factor is greater than about 1.2.

Preferably, the controller controls the laser to radiate a pulse of light only if a located feature occupies an area on the skin consistent with the size distribution of areas occupied on the skin by features to be treated.

In a preferred embodiment of the invention, the imaging subsystem scans an area of the skin and during scanning automatically locates features on the area to be treated.

In a preferred embodiment of the invention, the imaging subsystem comprises:

at least one photosensitive surface that generates signals responsive to an image formed thereon; and imaging optics that images light that it collects on the at least one photosensitive surface;

wherein, to scan the area, the imaging optics are moved relative to the skin so as to image regions in the scanned area onto the at least one photosensitive surface.

Preferably, the imaging optics has a focal point and the spot to which the pulse of laser light is focused is centered at the imaging optics focal point.

Preferably, the controller controls the laser to radiate a pulse of light only if a feature to be treated is determined to lie substantially within an area centered at the imaging optics focal point having a size substantially equal to the size of the spot to which the laser pulse is focused.

Preferably, the system includes circuitry that receives signals generated by the at least one photosurface responsive to an imaged region of the skin and processes the signals to locate contrasted sub-regions in the imaged region to locate features to be treated.

Preferably, the at least one photosensitive surface comprises a single photosensitive surface. Preferably, the photosensitive surface comprises a quadrature detector. Preferably signals from the quadrature detector are used to determine whether a contrasted sub-region imaged on the quadrature detector is substantially centered within the spot to which the laser pulse is focused. Preferably, signals from the quadrature detector are used to determine whether a contrasted sub-region imaged on the quadrature detector is larger than a predetermined minimum size consistent with the size distribution of areas occupied on the skin by features to be treated.

In a preferred embodiment of the invention, the photosensitive surface additionally comprises at least two photodetectors located adjacent to opposite sides of the quadrature detector. Preferably, if any of the photodetectors adjacent to sides of the quadrature detector generates a signal responsive to a contrasted sub-region imaged on the photosensitive surface, a portion of the sub-region is determined to lie outside the spot to which the laser pulse is focused and the laser is not energized.

In an alternative preferred embodiment of the invention, the at least one photosurface comprises a first and a second photosensitive surface. Preferably, the first photosensitive surfaces comprises a quadrature detector. Preferably, signals from the quadrature detector are used to determine whether a contrasted sub-region imaged on the quadrature detector is substantially centered within the spot to which the laser pulse is focused. Preferably, signals from the quadrature detector are used to determine whether a contrasted sub-region imaged on the quadrature detector is larger than a predetermined minimum size consistent with the size distribution of areas occupied on the skin by features to be treated.

In a preferred embodiment of the invention, the second detector comprises a photodetector having a mask that blocks light from impinging on an area located at it's center. Preferably, the photosensitive surface generates signals responsive to a contrasted sub-region imaged on the photosensitive surface, a portion of the sub-region is determined to lie outside of the spot to which the laser pulse is focused and the laser is not energized.

In a preferred embodiment of the invention, the imaging optics comprises an objective lens system having a focal point that collects light from regions imaged by the imaging subsystem and wherein the focal point of the imaging optics is the focal point of the objective lens system. Preferably, the laser optics comprises an ocular lens system that receives light collected by the objective lens system and images the received light on the at least one photosensitive surface. Preferably, the objective lens system is rotatable about an axis of rotation that intersects the optic axis of the objective lens system. Preferably, the laser optics comprises a collimating lens system that receives light radiated by the laser, which it collimates and transmits parallel to the axis of rotation. Preferably, the imaging optics comprises a reflector that reflects the collimated laser light towards the objective lens system along a direction parallel to the optic axis of the objective lens system so that the laser light is focused to a spot at the focal point of the objective lens system. In a preferred embodiment of the invention, the reflector is a beam splitter. Preferably, the ocular lens system and the at least one photosensitive surface are positioned on a side of the reflector opposite to the side of the reflector on which the objective lens system is located.

In an alternative preferred embodiment of the invention, the reflector is a mirror. Preferably, the ocular optics and the at least one photosensitive surface are stationary with respect to the axis of rotation. Preferably, the system a beam splitter positioned between the collimating lens and the mirror and wherein light collected by the objective optics is reflected by the mirror along the axis of rotation towards the beam splitter, which reflects some of the collected light incident on it towards the ocular lens system.

In a preferred embodiment of the invention, the system comprises a motor or actuator that is coupled to the objective lens system and rotates the objective lens system with an oscillatory motion about the axis of rotation, so that the objective focal point moves back and forth along a planar arc having a fixed length.

In a preferred embodiment of the invention, the imaging optics and the at least one photosensitive surface are mounted within a hand held unit. Preferably, the light source is mounted in or on the hand held unit. Preferably, the laser is mounted within the hand held unit. Preferably, the controller is mounted in the hand held unit. Preferably, the system comprises a power source mounted in the hand held unit.

There is further provided, in accordance with a preferred embodiment of the invention, a method for treating features on the skin of a patient with laser light comprising:

optically scanning the patient's skin to locate features to be treated; and during scanning, when a feature is located, focusing a pulse of laser light energy to a spot that covers substantially completely the feature, which spot has an area substantially equal to an area characteristic of the size distribution of areas occupied on the skin by features to be treated, multiplied by a factor greater than one, preferably, greater than about 1.2 and preferably less than about 1.5 or 2.

In a preferred embodiment of the invention, the method includes analyzing imaged regions of the skin to locate features to be treated. Preferably, analyzing imaged regions comprises determining whether an imaged region of the skin has a feature having a size consistent with the size distribution of areas occupied on the skin by features to be treated. Preferably, analyzing imaged regions comprises determining whether an imaged region of the skin has a hair feature to be treated located within a localized region on the skin which is centered at the focal point.

There is further provided, in accordance with a preferred embodiment of the invention, a method for depilating a patient's skin using laser light comprising:

optically scanning the patient's skin to locate hair follicles in regions of the skin to be depilated; and during scanning, when a hair follicle is located, cauterizing the hair follicle by focusing a pulse of laser light energy to a spot that shadows substantially completely the hair follicle, which spot has an area substantially equal to an area characteristic of the size distribution of areas occupied on the skin by hair follicles, multiplied by a factor greater than one, preferably greater than about 1.2, and preferably less than 1.5 or 2.

In a preferred embodiment of the invention, the method includes analyzing imaged regions of the skin to locate hair follicles to be treated. Preferably, analyzing imaged regions comprises determining whether an imaged region of the skin has a feature having a size consistent with the size distribution of follicles areas occupied on the skin by features to be treated. Preferably, analyzing imaged regions comprises determining whether an imaged region of the skin has a follicle to be treated located within a localized region on the skin which is centered at the focal point.

In a preferred embodiment of the invention, scanning comprises moving an optical imaging system having a focal point over the patients skin to image different regions of the skin. Preferably, moving an optical imaging system comprises moving the focal point close to and along the patient's skin.

Preferably, focusing a pulse of laser light energy comprises focusing the energy to a spot centered at the focal point.

In a preferred embodiment of the invention, the localized region is substantially equal to the size of the spot to which the laser light is focused. Preferably, moving the focal point comprises moving the focal point with an oscillatory motion along a first direction on the skin. Preferably, the method includes moving the focal point in a second direction substantially perpendicular to the first direction while the focal point is oscillating. Preferably, moving the optical imaging system comprises moving the optical imaging system by hand.

BRIEF DESCRIPTION OF FIGURES

The invention will be more clearly understood by reference to the following description of preferred embodiments thereof read in conjunction with the figures attached hereto. In the figures identical structures, elements or parts which appear in more than one figure are labeled with the same numeral in all the figures in which they appear. Dimensions of components and features shown in the figures are chosen for convenience and clarity of presentation and are not necessarily shown to scale. The figures are listed below.

DETAILED DESCRIPTION OF PREFERRED EMBODIMENTS

Figure 1A:
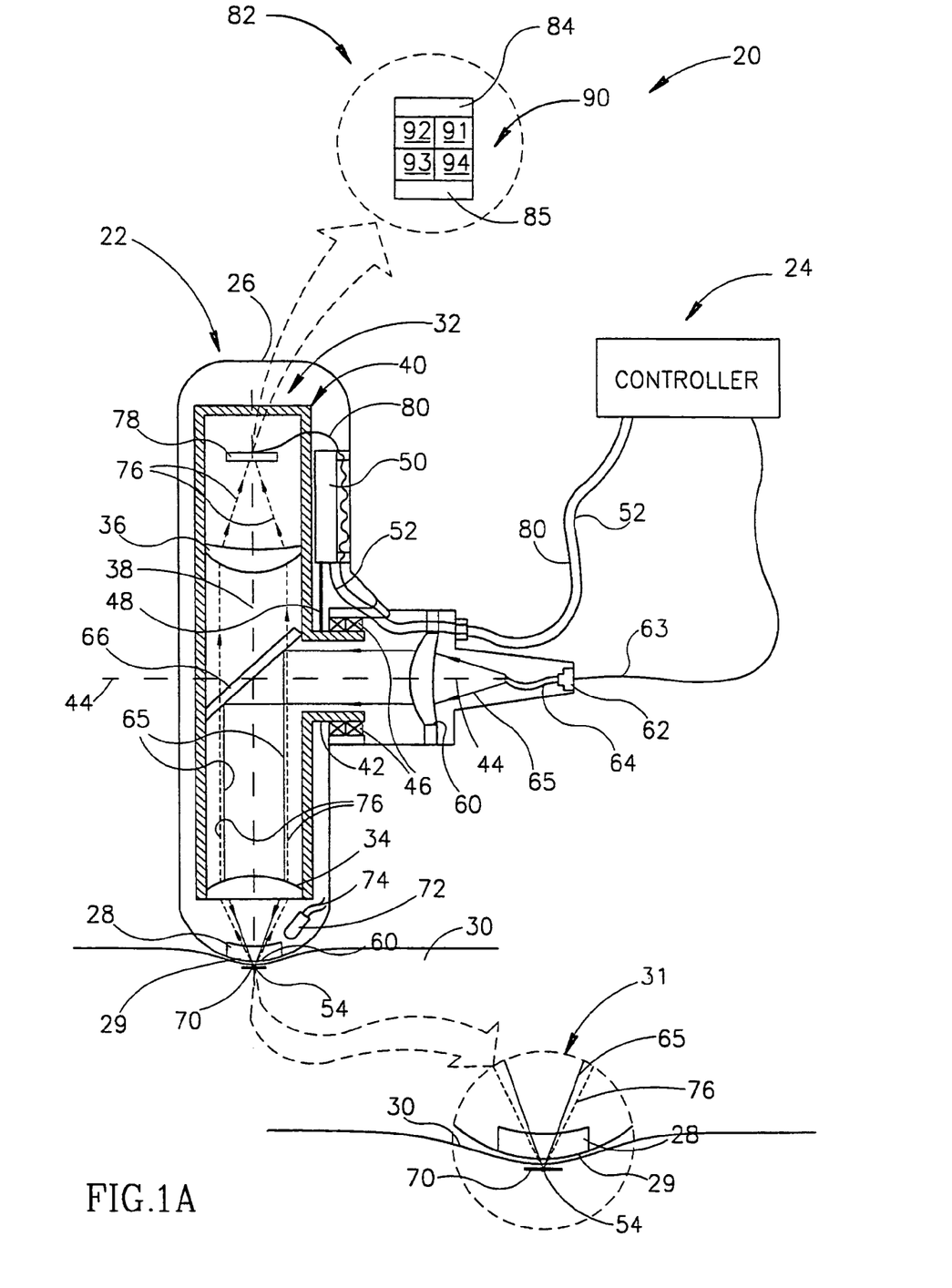
FIG. 1A shows schematically a laser system comprising a hand unit shown in cut-away side view, in accordance with a preferred embodiment of the present invention.

FIG. 1A schematically shows a laser system 20, in accordance with a preferred embodiment of the present invention, comprising a hand unit 22 and a controller 24. Hand unit 22 is shown in a cutaway cross-section view. It should be noted that whereas controller 24 is shown separate from hand unit 22, in most preferred embodiments, controller 24 is mounted on or inside hand unit 22. In addition, energy to power hand unit 22 may come from an external power supply or preferably from an appropriate portable power supply mounted inside hand unit 22.

Hand unit 20 preferably comprises a housing 26 having a window 28. Window 28 has a surface 29 that is pressed to the skin 30 of a patient. Surface 29 and skin 30 are shown separated by a small distance for clarity of presentation and are shown magnified in an insert 31. Hand unit 20 comprises a microscope 32 mounted inside housing 26. Microscope 32 comprises an objective lens 34, an ocular lens 36 and an optic axis 38. Objective lens 34 and ocular lens 36 are preferably mounted in a microscope housing 40. Whereas microscope 32 is shown comprising only two lenses, a hand unit in accordance with a preferred embodiment may comprise a microscope having more than two lenses. For example, the ocular and/or the objective may comprise a system of lenses.

Microscope housing 40 preferably has a circularly cylindrical tubular extension 42 having an axis of rotation 44 that preferably intersects optic axis 38 at 90°. Microscope 32 is preferably rotatably mounted to hand unit 22 by mounting tubular extension 42 to a bearing 46 that is fastened to housing 26 of hand unit 22. Bearing 46 preferably enables microscope 32 to be rotated back and forth about axis of rotation 44 but prevents motion of microscope 32 parallel to axis of rotation 44. Preferably microscope 32 is controlled to rotate back and forth about axis 44 with an oscillating motion having predetermined angular amplitude. Preferably the frequency of oscillation is less than 100 HZ. More preferably, the frequency of oscillation is less than 50 Hz. Most preferably the frequency is between 5 and 20 Hz.

Many methods for achieving the oscillatory motion are known in the art and may be used in accordance with preferred embodiments of the present invention for providing such motion to microscope 32. For example, in some preferred embodiments of the present invention a electromotor or piezoelectric micromotor is pressed to the surface of tubular extension 42, and thereby microscope 32, to rotate tubular extension 42 back and forth about axis of rotation 44. In some preferred embodiments of the present invention tubular extension 42 is coupled by an appropriate mechanical drive train to a motor or actuator that rotates tubular extension 42 in an oscillatory motion.

By way of example, in FIG. 1A tubular extension 42 is shown having an arm 48 that is rotated back and forth by a motor 50 in order to oscillate microscope 32. Arm 48 is mechanically coupled to motor 50, using any of many various mechanical configurations (not shown) known in the art, such as by a crank and crankshaft. Preferably motor 50 is controlled and powered by controller 24 to which motor 50 is connected by an appropriate power and control line 52.

The size of window 28, its relative position with respect to microscope 32 and the amplitude of motion of microscope 32 are preferably such that for each angular position of microscope 32 about axis 44, optic axis 38 passes through window 28. Microscope 32 has a focal point 54, preferably located a short distance below window 28. Focal point 54 is most clearly shown in insert 31. As a result of the oscillating motion of microscope 32, focal point 54 moves back and forth along a circular arc (not shown), which is perpendicular to the plane of FIG. 1A and which lies in a plane perpendicular to axis 44. The projection of focal point 54 on skin 30 oscillates back and forth and scans skin 30 along a substantially straight line perpendicular to the plane of FIG. 1A (and of course axis 44). Preferably, surface 29 of window 28 is curved in the plane of the arc of motion of focal point 54 so that focal point 54 is substantially a same distance from surface 29 for all points along its arc of motion.

Hand unit 22 preferably comprises a laser 62 and a collimating lens 60 having an optic axis coincident with axis of rotation 44. Laser 62 is turned on and off by controller 24 to which laser 62 is connected via a control line 63. Laser light from laser 62 is preferably piped to collimating lens 60 via a light guide 64. The laser light is represented by lines 65 that have arrows indicating the direction of travel of the laser light. Collimating lens 60 collimates laser light 65 and directs the collimated laser light to a beam splitting mirror 66 located between objective and ocular lenses 34 and 36. Beam splitter 66 directs some of laser light 65 in a direction parallel to optic axis 38 towards objective lens 34, which focuses laser light 65 to a spot 70 (shown in cross section) centered on focal point 54. Spot 70 and its relationship to focal point 54 is most clearly shown in insert 31.

Preferably laser 62 is a laser diode or an array of a plurality of laser diodes. Light guide 64 preferably comprises a fiber optic bundle. Preferably, laser 62 and light guide 64 are matched so that their throughput is such that spot 70 has a size slightly larger than a characteristic size of a target being treated with laser system 20. (The throughput of the combination of laser 62 and light guide 64 is the product of the cross sectional area of light guide 64 and the angular divergence of laser light exiting the output end of light guide 64.) For example, assume that laser system 20 is being used to remove hair from skin 30 by cauterizing hair follicles with laser energy. Hair follicles have an average diameter of about 200 microns. Therefore, the throughput of laser 62 and light guide 64 is preferably determined so that spot size 70 has a diameter of about 250 microns. This choice for spot size assures efficient cauterization of hair follicles having a diameter of 200 microns without irradiation of large areas of skin 30 surrounding hair follicles that are cauterized.

Hand unit 22 preferably comprises a light source 72 that radiates light through window 28 to illuminate regions of skin 30 located in the vicinity of focal point 54. In some preferred embodiments of the present invention light source 72 comprises a LED or a low powered laser having a spectrum that enhances contrast between features to be irradiated and clear skin.

Preferably, light source 72 comprises a white light source (not shown) that radiates white light onto a preferably adjustable spectrometer (not shown). The adjustable spectrometer, comprising an appropriate diffraction grating or prism, determines the spectral distribution of light from the white light source that is radiated by light source 72 to illuminate skin 30. Light source 72 is preferably connected to controller 24 by an appropriate control line 74 (only part of which is shown). Preferably, controller 24 controls the spectrometer so that light source 72 radiates light through window 28 that has a spectral distribution which enhances contrast between features of skin 30 to be treated and skin tissue that is free of the features to be treated. For example, if skin 30 is to be depilated, preferably skin 30 is first shaved and light source 72 is controlled to illuminate skin 30 with light having a spectral distribution that enhances the contrast between hair follicles of the shaved hairs and hairless skin.

Objective lens 34 collects light from light source 72 that is reflected by a region of skin 32 substantially centered at focal point 54 and directs the collected light, towards ocular lens 36. The reflected light is represented by dashed lines 76, which have arrows to indicate the direction of travel of the reflected light. Some of light 76 is transmitted by beam splitter 66 to ocular lens 36, which focuses light 74 to form an image of the region on a photosensitive surface 78.

Photosensitive surface 78 generates signals responsive to the image and the signals are preferably transmitted to controller 24 via a data line 80. Controller 24 comprises circuitry that analyzes the signals to determine if a feature to be treated with laser light is imaged on photosensitive surface 78. If such a feature is found and is localized within an area centered on focal point 54 that has a size substantially equal to the size of spot 70, the region is determined to have a target. For example, if hair follicles are being treated, controller 24 "searches" for a localized dark or light (depending upon the spectrum of light from light source 72) area set against a bright or dark background respectively that has a size characteristic of a hair follicle. If such an area is found and it is substantially localized within an area centered at focal point 54 having the size and shape of spot 70 it is determined to be a target.

Different types of photosensitive surfaces known in the art are useable as photosensitive surface 78. For example, in some preferred embodiments of the present invention photosensitive surface 78 comprises a pixelated photosensitive surface such as a CCD camera. In these embodiments a relatively detailed image of a region centered on the focal point is acquired and analyzed. In other more preferred embodiments of the present invention photosensitive surface 78 comprises a relatively small number of photodetectors in an array appropriate for determining whether a feature is a target or not.

A version of photosensitive surface 78 based on quadrature detection is shown in insert 82. Photosensitive surface 78 preferably comprises photodetectors 84 and 85 and a quadrature detector 90 comprising photodetectors 91, 92, 93 and 94 and having a center point. Axis 38 intersects photosensitive surface 78 at its center point. When a feature that might represent a feature to be treated with laser light is imaged on photosensitive surface 78, signals from photodetectors 91, 92, 93 and 94 are processed using algorithms known in the art to estimate the location of the feature with respect to focal point 54. Signals from photodetectors 84 and 85 are used to determine if the imaged feature occupies an area on the skin greater than a predetermined maximum area. If the image of the feature on photosensitive surface 78 simultaneously stimulates either of photodetectors 84 and 85, the feature is determined by controller 24 to be outside the area of quadrature detector 90 or have an area greater than the maximum area. If the feature is determined to be smaller than the maximum area (i.e. neither of photodetectors 84 and 85 is stimulated) and its centroid is determined to be within a predetermined maximum distance from focal point 54, then the feature is a target to be irradiated with laser light. The maximum area and maximum distance are preferably chosen to assure that the feature lies substantially within an area centered at focal point 54 whose size is substantially equal to the size of spot 70. Once a target is determined to be imaged on photosensitive surface 78, controller 24 controls laser 62 to radiate a pulse of light that is focused to spot 70 and deposits a desired amount of energy on the target.

Figure 1B:
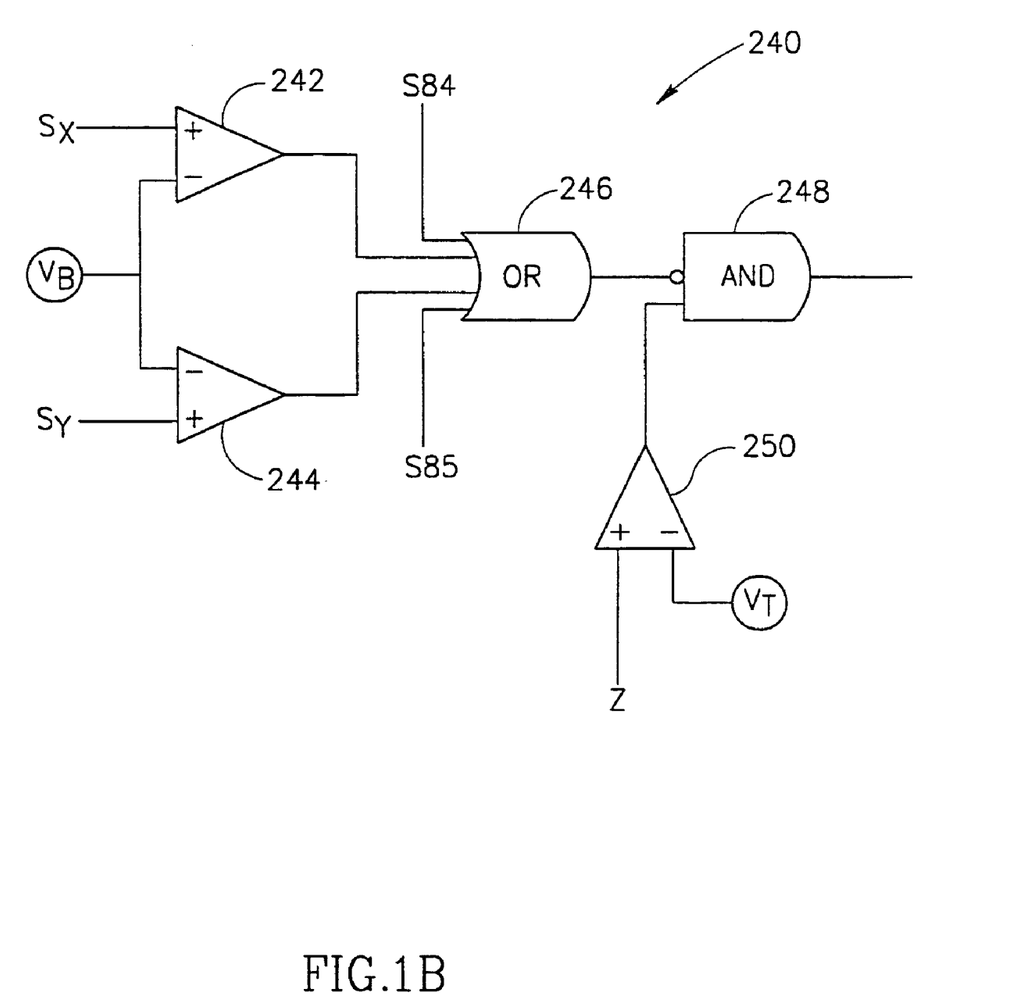
FIG. 1B shows a schematic circuit for analyzing images of regions of a patient's skin formed on a photosensitive surface located in the hand unit shown in FIG. 1A, in accordance with a preferred embodiment of the present invention.

FIG. 1B shows a schematic circuit 240 that illustrates how signals from photosurface 78 shown in insert 82 are used to determine whether or not to energize laser 62.

Let S84, S85, S91, S92, S93, and S94 represent signals received from detectors 84, 85, 91, 92, 93 and 94 respectively. Define a sum signal Z=(S91+S92+S93+S94). The magnitude of Z is a measure of the total amount of light received by photosensitive surface 78 from a feature imaged on photosensitive surface 78. Sum signal Z is used to determine whether or not a prospective feature for treatment is imaged on photosensitive surface 78 and to normalize signals from the individual detectors 91–94. In order to energize laser 62 the sum signal Z must be larger than a predetermined threshold, i.e. there must be a feature to be treated imaged on photosensitive surface 78 and the feature must be larger than a predetermined size as determined by the threshold.

Define $S_X=|(S91+S94)-(S92+S93)|/Z$ and $S_Y=|(S91+S92)-(S93+S94)|/Z$. The magnitudes of $S_X$ and $S_Y$ indicate respectively how far off center the centroid of the imaged feature is from focal point 54 along two orthogonal "X" and "Y" directions. For a feature whose centroid is substantially located at focal point 54, $S_X$ and $S_Y$ are substantially equal to zero.

Circuit 240 comprises two comparators 242 and 244 for comparing $S_X$ and $S_Y$ to a voltage $V_B$. Signals $S_X$ and $S_Y$ are input to the plus inputs of comparators 242 and 244 respectively. Comparators 242 and 244 generate output signals only if $S_X$ and $S_Y$ respectively are greater than the bias voltage $V_B$.

The outputs of comparators 242 and 244 are input to a four way OR circuit 246. Signals S84 and S85 are also input to OR circuit 246. OR circuit 246 generates an output signal if either S84 or S85 is non-zero or if there is a signal from either comparator 242 or 244. The output of OR circuit 246 is input to AND circuit 248 after being inverted.

Sum signal Z is input to a comparator 250 that compares sum signal Z to a threshold voltage VT. The output of comparator 250 is input to AND circuit 248. AND circuit 248 receives a signal from comparator 250 only if the sum signal Z is larger than VT.

AND circuit 248 therefore generates a signal only if a feature of sufficient size is imaged on photosensitive surface 78, as indicated by sum signal Z, and only if there are no signals from detector 84 detector 85, comparator 242 and comparator 244. If there is an output signal from AND circuit 248 laser 62 is energized.

It is seen that $V_B$ determines upper limits in the X and Y directions for the displacement of the centroid of a feature imaged on photosensitive surface 78. If $S_X$ and $S_Y$ are greater than $V_B$, the imaged feature is determined to be too far off center or too large to be an acceptable target for irradiation with laser light and AND circuit 248 will not generate an output signal.

It should be noted that circuit 240 assumes that a feature to be irradiated is brighter than background skin. A similar circuit (in which for example $S_X$, $S_Y$, S84 and S85 are inverted) is used for processing images from photosensitive surface 78 if a feature to be irradiated is darker than the background skin.

Preferably, hand unit 22 comprises sensors (not shown) that detect whether or not window 28 is pressed to a patient's skin. Preferably, the sensors are pressure sensors that provide output signals responsive to pressure on window 28. Preferably, laser 62 is energized only if the output signals indicate that window 28 is being pressed to a patient's skin.

Preferably, circuitry that analyzes signals from photosensitive surface 78 to "acquire a target" and energize laser 62 performs these tasks in a time that is short compared to a "spot crossing time" i.e. the diameter of spot 70 divided by the scanning speed of focal point 54. As a result, signal analysis and target acquisition is performed, in accordance with a preferred embodiment of the present invention, continuously, substantially in real time.

Assume that microscope 32 oscillates with a frequency of 20 cps and that the amplitude of motion of focal point 54 is 2.5 cm. Focal point 54 therefore scans the skin with a velocity of 100 cm/s. If the size of spot 70 is 200 microns then the spot crossing time is $2 \times 10^{-4}$ sec. Real time target acquisition and laser energizing is therefore easily accomplished, in accordance with a preferred embodiment of the present invention, using nanosecond circuitry and possibly even microsecond circuitry.

Whereas hand unit 22 comprises light source 72 for illuminating a patient's skin, in some preferred embodiments of the present invention light from laser 62 is used to illuminate the patient's skin. During scanning, laser 62 is not turned off but radiates light at low intensity, which is focused at focal point 54. The low intensity laser light is used to image the patient's skin. When a target is located, controller 24 controls laser 62 to increase the intensity of the laser light that it radiates and send a pulse of laser light that deposits a desired amount of energy on the target.

Figure 2:
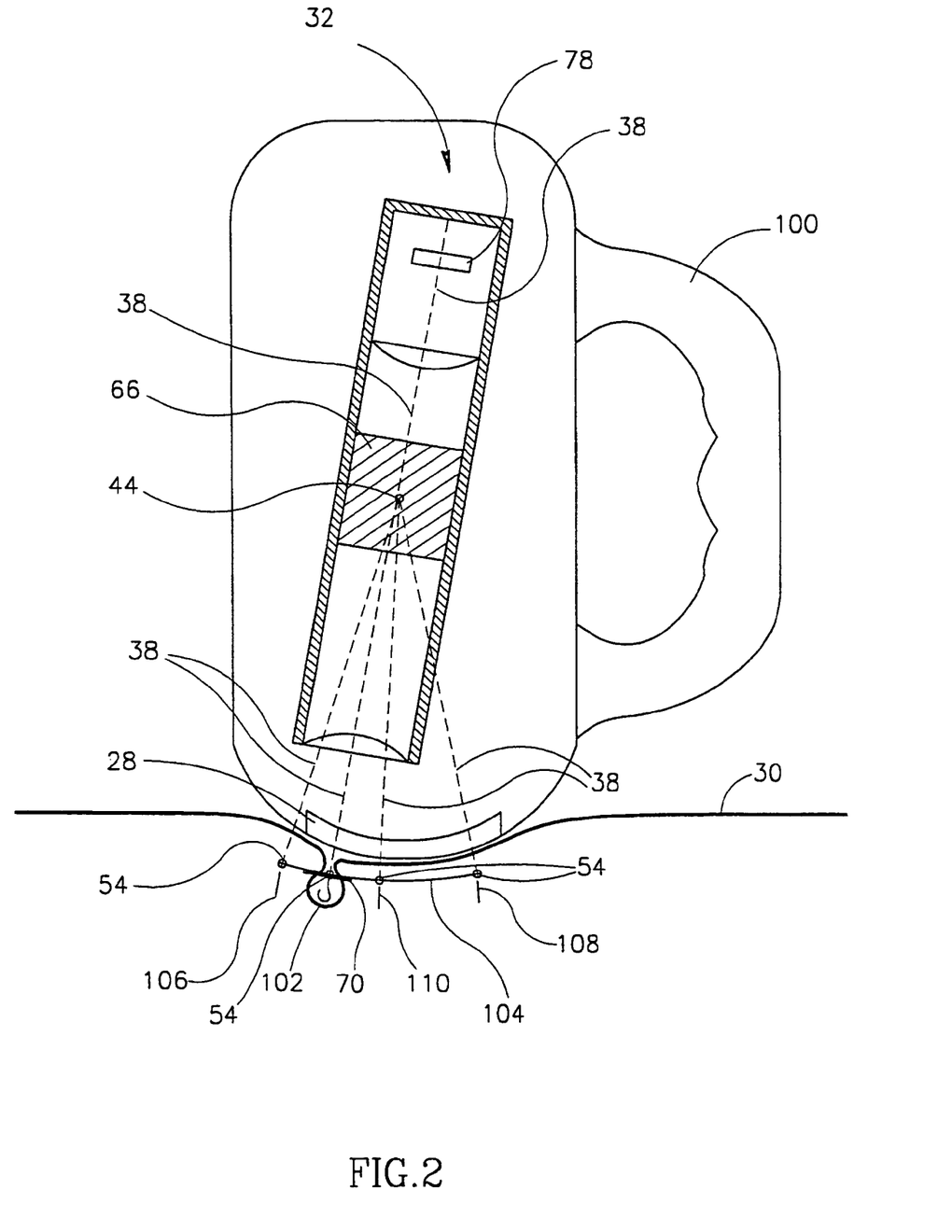
FIG. 2 shows schematically the hand unit shown in FIG. 1A in a cut-away front view.

FIG. 2 schematically shows hand unit 22, which is shown FIG. 1A, in a cutaway view from a direction parallel to axis of rotation 44 shown in FIG. 1A. In FIG. 2, axis of rotation 44 is represented by a point 44 and beam splitting mirror 66 (FIG. 1A) occupies a shaded area labeled 66. Preferably, hand unit 22 comprises a handle 100. Skin 30 is schematically shown with a hair follicle 102. As a result of the pressure of window 28 on skin 30, skin 30 deforms slightly and molds itself to the shape of surface 29 of window 30. This assures that focal point 54 is properly positioned with respect to the surface of skin 30.

Oscillatory rotation of microscope 32 about axis of rotation 44 results in oscillatory motion of focal point 54 in the plane of FIG. 2 along an arc 104. Focal point 54 is shown in a number of different positions in FIG. 2. Short witness lines 106 and 108 indicate extreme positions of focal point 54 at the ends of arc 104. A witness line 110 marks the central position of the motion of focal point 54. Part of optic axis 38 is shown for the positions marked by the witness lines.

Microscope 32 is shown at a point of its motion about axis of rotation 44 at which focal point 54 is positioned at the location of hair follicle 102. At this position microscope 32 images hair follicle 102 on photosensitive surface 78 and controller 24 (FIG. 1A) determines that there is a target at focal point 54. Laser 62 (FIG. 1A) is controlled to radiate a pulse of light that is focused to spot 70 to coagulate follicle 102.

Figure 3:
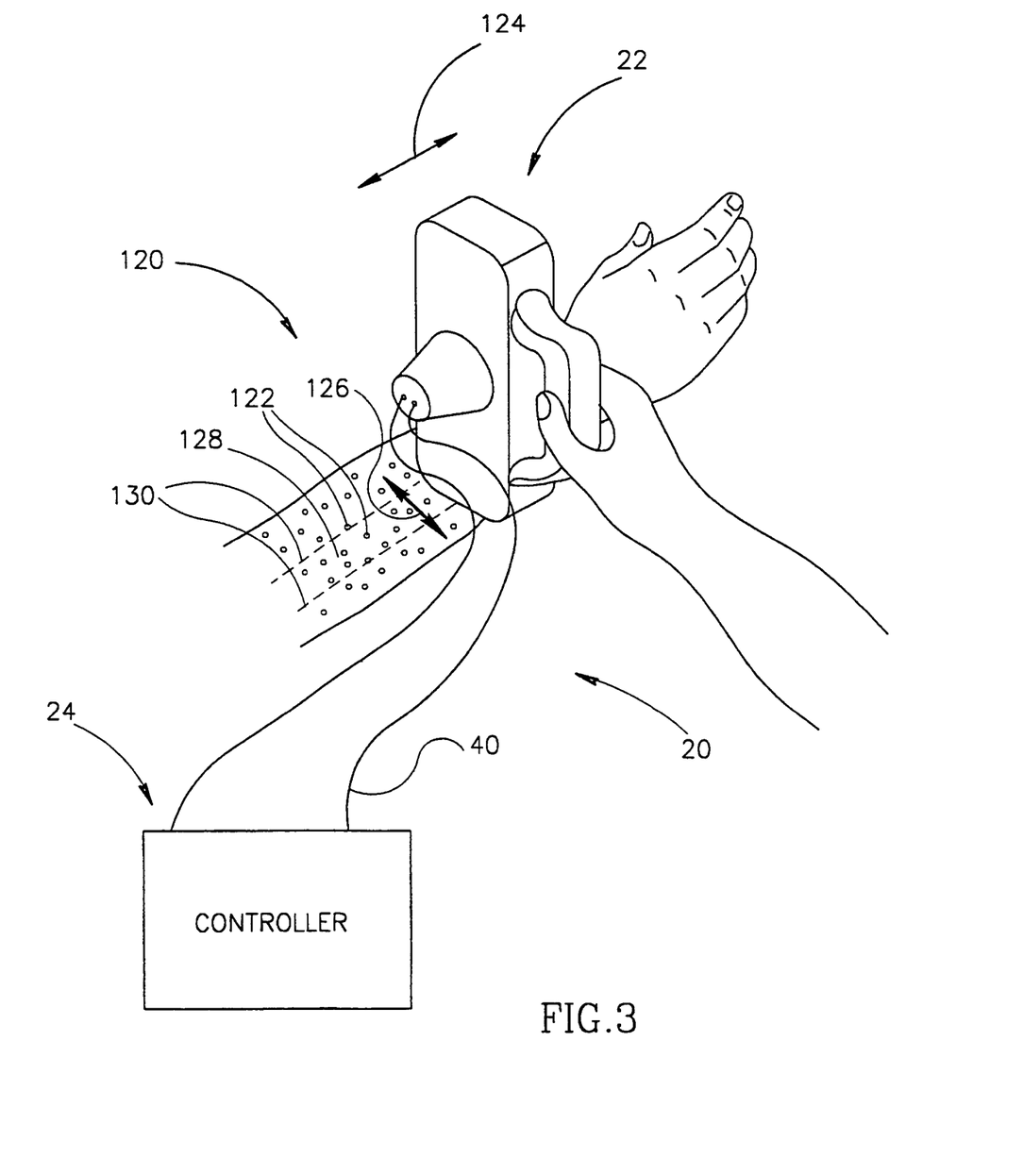
FIG. 3 shows schematically the laser system being used to remove hair from the arm of a patient, in accordance with a preferred embodiment of the present invention.

Whereas in hand unit 22 oscillatory motion of focal point 54 is achieved by rotating microscope 32, in some preferred embodiments of the present invention oscillatory motion of focal point 54 is achieved by rotating mirror 66. In some preferred embodiments mirror 66 is rotated about axis of rotation 44. In some preferred embodiments of the present invention mirror 66 is rotated about an axis perpendicular to axis of rotation 44 and optic axis 38 that passes through their intersection. FIG. 3 schematically shows laser system 20 being used to depilate skin on an arm 120 of a patient, in accordance with a preferred embodiment of the present invention. The skin on arm 120 is preferably shaved to reveal hair follicles 122 (shown schematically with greatly exaggerated size) that are to be cauterized with laser light radiated from hand unit 22.

Hand unit 22 is held so that window 28 (shown in FIGS. 1 and 2) is pressed to the surface of the skin of arm 120. With the surface of window 28 in contact with the patient's skin, hand unit 22 is moved back and forth along arm 120 in a direction indicated by double arrow line 124. Preferably, double arrow line 124 is substantially parallel to axis of rotation 44 of microscope 32, which is mounted inside hand unit 22 (FIGS. 1 and 2). The oscillatory motion of microscope 32, causes focal point 54 (FIGS. 1 and 2) of the microscope to move back and forth on the skin along a direction indicated by double arrow line 126. Double arrow line 126 is substantially perpendicular to double arrow line 124.

As a result of the motion of focal point 54 in the direction of line 126 in combination with the displacement of hand unit 22 along the direction of line 124, substantially all of a strip 128 of skin located between lines 130 is scanned for hair follicles 128. When these are located they are treated with laser light as described above. The width of strip 128 is substantially equal to the extent of motion of focal point 54 on the skin of arm 120. The length of strip 128 is equal to a distance that hand unit 22 is moved along the direction of double arrow line 30.

Figure 4:
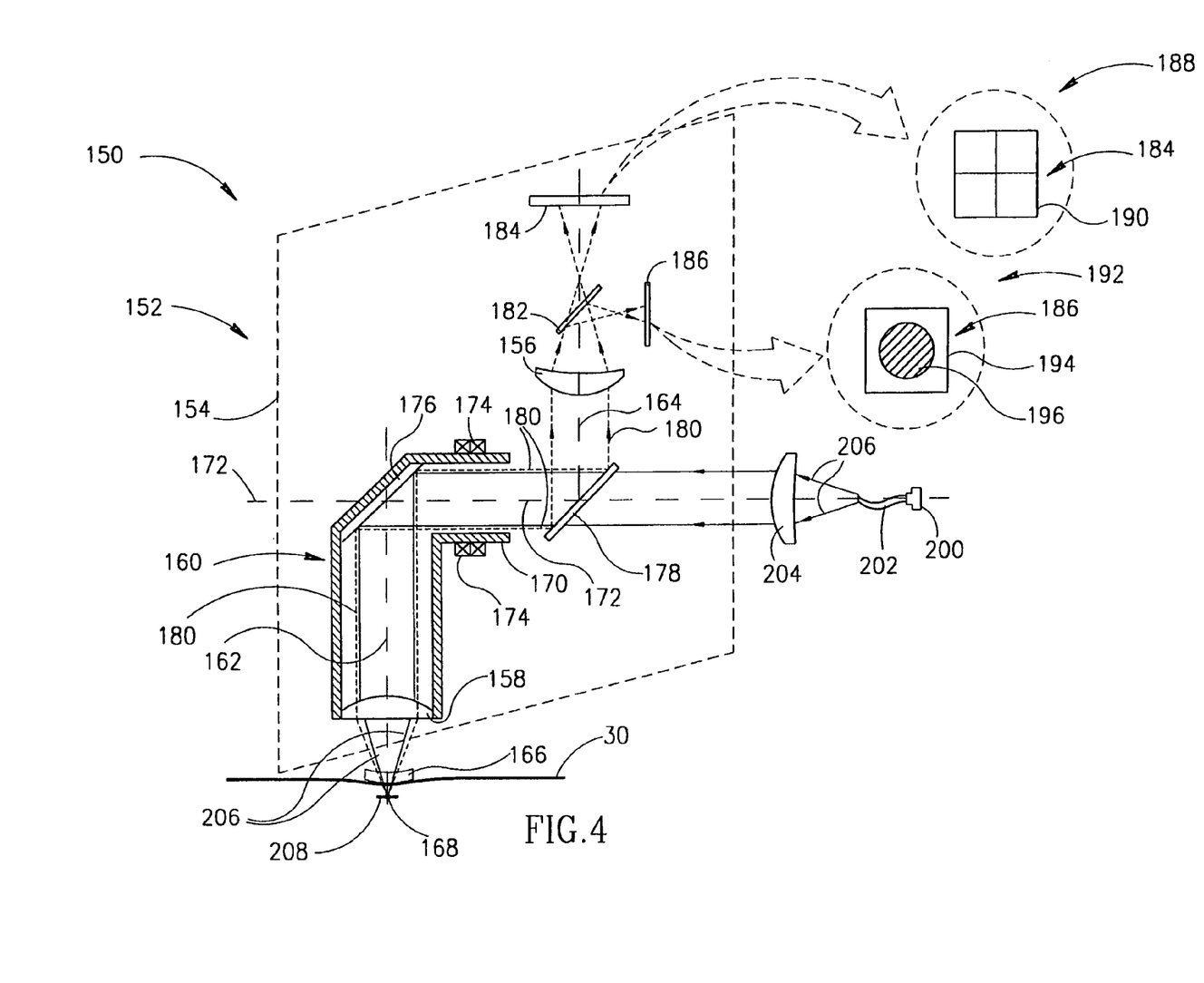
FIG. 4 shows schematically a variation of the hand unit shown in FIGS. 1–3, in accordance with a preferred embodiment of the present invention.

FIG. 4 schematically shows a hand unit 150 that is a variation of hand unit 22 shown in FIGS. 1–3. Hand unit 150 is shown in a cutaway cross sectional view. Hand unit 150 preferably has a housing, which is not shown in FIG. 4 for clarity of presentation. In hand unit 22 all the optical elements of a microscope are comprised in a single rotating housing. Hand unit 150 on the other hand comprises a microscope 152 in which some of the optical components are mounted in a housing rotatable with respect to the hand unit housing and others are preferably fixed to the hand unit housing.

Components of microscope 152 are shown within dotted boundary curve 154. Microscope 152 has an ocular lens 156 mounted to the housing of hand unit 150 in a fixed position and an objective lens 158 comprised in an elbow shaped housing 160. Objective and ocular lenses 158 and 156 have optical axes 162 and 164 respectively. Objective lens 158 collects light from regions of a patient's skin 30 through a window 166 in the hand unit housing and has a focal point 168 located slightly below window 166.

Elbow housing 160 preferably has a circularly cylindrical tubular extension 170 having an axis of rotation 172. Axis of rotation 172 preferably intersects optic axes 162 and 164 at substantially 90°. Tubular extension 170 is mounted to a bearing 174 that is fastened to the hand unit housing. Bearing 174 enables tubular extension 170 to rotate about axis of rotation 172 but preferably prevents tubular extension 172 from moving parallel to axis 172. Tubular extension 170 is coupled to an appropriate motor or actuator (not shown) and rotated in an oscillatory motion about axis of rotation 172 similarly to the way in which tubular extension 42 of microscope 32 is rotated about axis of rotation 44. Focal point 168 therefore oscillates about axis of rotation 172 along an arc (not shown) in the same manner in which focal point 54 of hand unit 22 oscillates about axis of rotation 44 along arc 104 (FIG. 2).

Elbow housing 160 preferably comprises a mirror 176 that reflects light collected by objective 158 to a beam splitter 178. The light is represented by lines 180 having arrows thereon that indicate the direction in which the light travels. Beam splitter 178 reflects some of light 180 to ocular lens 156. Ocular lens 156 focuses and preferably directs light 180 towards a beam splitter 182 that transmits some of the light to a photosensitive surface 184 and reflects some of the light to a photosensitive surface 186.

Photosensitive surface 184, which is shown in plan view in insert 188, preferably comprises a quadrant detector 190 that is used to determine the position relative to focal point 168 of a prospective feature for laser treatment on the skin of a patient. Photosensitive surface 186, which is shown in insert 192, preferably comprises a detector 194 having a mask 196 located at the center of detector 194. Light incident on mask 196 does not reach detector 194. Detector 194 is preferably used to determine if the size of a prospective feature for laser treatment on a patient's skin is larger than a predetermined size. If a prospective feature is centered at focal point 168 its image will be centered on each of photosensitive surfaces 184 and 186. If the feature is larger than a predetermined maximum size, its image will be larger than mask 196 and detector 194 will generate signals responsive to the image indicating that the image is larger than the mask and therefore larger than the predetermined maximum size. In some preferred embodiments of the present invention quadrature detector 190 has a mask that covers all of quadrature detector 190 except for a region in the center preferably having the same area as mask 196. Masking quadrature detector 190 in this manner increases signal to noise from quadrature detector 190.

Signals generated by photodetectors in detectors 190 and 194 responsive to images of a prospective feature for laser treatment formed on photosensitive surfaces 184 and 186 respectively are transmitted to a controller (not shown). The controller analyzes the signals to determine if the feature is a target to be treated with laser light. In order for a feature to be a target, preferably the location of its centroid, as determined using signals from quadrature detector 190, must lie within a predetermined distance of focal point 168. In addition, preferably the size of the feature, as determined using signals from masked detector 194, must be less than the predetermined maximum size. Hand unit 150 comprises a laser 200 that is controlled by the controller. As in laser system 20 shown in FIGS. 1–3, when a target is identified, the controller controls laser 200 to radiate a pulse of laser light to irradiate the target. Laser light radiated from laser 200 is piped by a light guide 202 to a collimating lens 204 that transmits the laser light to beam splitter 178. The laser light is represented by lines 206 having arrows thereon that indicate the direction of travel of the laser light. Some of laser light 206 is transmitted by beam splitter 178 to mirror 176, which reflects laser light 180 to objective lens 158. Objective lens 158 focuses the laser light to a spot 208. The predetermined maximum distance, maximum size and the size of spot 208 are preferably determined responsive to the size of a feature to be treated with laser light so that when a feature is determined to be a target, spot 208 will substantially cover all of the target.

In the description and claims of the present application, each of the verbs, "comprise" "include" and "has", and conjugates thereof, are used to indicate that the object or objects of the verb are not necessarily a complete listing of components, elements or parts of the subject or subjects of the verb.

The present invention has been described using non-limiting detailed descriptions of preferred embodiments thereof that are provided by way of example and are not intended to limit the scope of the invention. Variations of embodiments described will occur to persons of the art. For example, in some preferred embodiments of the present invention the hand unit comprises a processor for processing data from photosensitive surfaces and determining whether a feature on the skin of a patient is a target. Whereas, oscillatory motion of the focal points of a microscope in a hand units has been described as resulting from rotational motion of the microscope the motion can be also be achieved by linear motion of the microscope. Furthermore, different configurations of photodetectors on photosensitive surfaces, other than those described, can also be used for locating and sizing prospective targets for laser treatment, and these will occur to a man of the art. The scope of the invention is limited only by the following claims.

The invention claimed is:

1. A laser system for treating features on the skin of a patient with laser light comprising:
   an imaging subsystem comprising:
      at least one photosensitive surface;
      an objective lens system having a focal point and optic axis;
      a motor or actuator that rotates the objective lens system about an axis that intersects the optic axis so that the focal point moves back and forth with an oscillatory motion along a planar arc to scan a region of the skin;
      an ocular lens system that uses light from the objective lens system to image sub-regions of the scanned region on the at least one photosurface; and
      a controller configured to automatically determine, responsive to the images, if a sub-region comprises a feature on the skin to be treated and if so, a location of the feature in the region;
   a laser; and
   laser optics that focuses light from the laser onto a feature located by the imaging subsystem; wherein the controller, controls the laser to radiate a pulse of laser light that is focused by the laser optics to a spot localized about the feature.

2. A laser system according to claim 1 comprising a light source that illuminates regions imaged by the imaging subsystem with light for which the features to be treated have a reflectance different from that of clear skin so that a feature to be treated appears as a contrasted sub-region of an imaged region of the skin.

3. A laser system according to claim 2 wherein the spectrum of the light radiated by the light source is tunable.

4. A laser system according to claim 1 wherein the spot to which the laser is focused has an area having a diameter substantially equal to a diameter of an area occupied on the skin by a feature to be treated, multiplied by a factor greater than one.

5. A laser system according to claim 4 wherein the factor is less than 2.

6. A laser system according to claim 4 wherein the factor is less than 1.5.

7. A laser system according to claim 4 wherein the factor is greater than about 1.2.

8. A laser system according to claim 1 wherein the spot to which the pulse of laser light is focused is centered at the focal point of the objective lens system.

9. A laser system according to claim 8 wherein the controller controls the laser to radiate a pulse of light only if a feature to be treated is determined to lie substantially within the spot to which the laser pulse is focused.

10. A laser system according to claim 1 wherein the controller processes the images to locate contrasted sub-regions in the imaged skin region to determine if the region comprises a feature to be treated.

11. A laser system according to claim 10 wherein the at least one photosensitive surface comprises a single photosensitive surface.

12. A laser system according to claim 11 wherein the photosensitive surface comprises a quadrature detector.

13. A laser system according to claim 12 wherein signals from the quadrature detector are used to determine whether a contrasted sub-region imaged on the quadrature detector is substantially centered within the spot to which the laser pulse is focused.

14. A laser system according to claim 12 wherein signals from the quadrature detector are used to determine whether a contrasted sub-region imaged on the quadrature detector is larger than a predetermined minimum size consistent with the size distribution of areas occupied on the skin by features to be treated.

15. A laser system according to claim 12 wherein the photosensitive surface additionally comprises at least two photodetectors located adjacent to opposite sides of the quadrature detector.

16. A laser system according to claim 15 wherein if any of the photodetectors adjacent to sides of the quadrature detector generates a signal responsive to a contrasted sub-region imaged on the photosensitive surface, the controller determines that a portion of the sub-region lies outside the spot to which the laser pulse is focused and the laser is not energized by the controller.

17. A laser system according to claim 10 wherein the at least one photosurface comprises a first and a second photosensitive surface.

18. A laser system according to claim 17 wherein the first photosensitive surfaces comprises a quadrature detector.

19. A laser system according to claim 18 wherein the controller processes signals from the quadrature detector to determine whether a contrasted sub-region imaged on the quadrature detector is substantially centered within the spot to which the laser pulse is focused.

20. A laser system according to claim 18 wherein the controller uses signals from the quadrature detector to determine whether a contrasted sub-region imaged on the quadrature detector is larger than a predetermined minimum size consistent with the size distribution of areas occupied on the skin by features to be treated.

21. A laser system according to claim 17 wherein the second detector comprises a photodetector having a mask that blocks light from impinging on an area located at it's center.

22. A laser system according to claim 21 wherein if the photosensitive surface generates signals responsive to a contrasted sub-region imaged on the photosensitive surface, the controller determines that a portion of the sub-region lies outside of the spot to which the laser pulse is focused and the laser is not energized by the controller.

23. A laser system according to claim 1 wherein the laser optics comprises a collimating lens system that receives light radiated by the laser, which it collimates and transmits parallel to the axis of rotation.

24. A laser system according to claim 23 wherein the imaging optics comprises a reflector that reflects the collimated laser light towards the objective lens system along a direction parallel to the optic axis of the objective lens system so that the laser light is focused to a spot at the focal point of the objective lens system.

25. A laser system according to claim 24 wherein the reflector is a beam splitter.

26. A laser system according to claim 25 wherein the ocular lens system and the at least one photosensitive surface are positioned on a side of the reflector opposite to the side of the reflector on which the objective lens system is located.

27. A laser system according to claim 24 wherein the reflector is a mirror.

28. A laser system according to claim 27 wherein the ocular optics and the at least one photosensitive surface are stationary with respect to the axis of rotation.

29. A laser system according to claim 28 comprising a beam splitter positioned between the collimating lens and the mirror and wherein light collected by the objective optics is reflected by the mirror along the axis of rotation towards the beam splitter, which reflects some of the collected light incident on it towards the ocular lens system.

30. A laser system according to claim 1 wherein the imaging optics and the at least one photosensitive surface are mounted within a hand held unit.

31. A laser system according to claim 30 wherein the light source is mounted in or on the hand held unit.

32. A laser system according to claim 30 wherein the laser is mounted within the hand held unit.

33. A laser system according to claim 30 wherein the controller is mounted in the hand held unit.

34. A laser system according to claim 30 comprising a power source mounted in the hand held unit.

35. A laser system for treating features on the skin of a patient with laser light comprising:
- a light source for illuminating the skin;
- at least one photosurface that generates signals responsive to light incident thereon;
- optics that automatically scans a focal region of the optics over the patient's skin and images light from the light source reflected by the skin on the at least one photosurface;

a motor or actuator that rotates at least a portion of the optics with an oscillatory motion so that the focal region moves back and forth along a planar are having a fixed length to scan the focal region over the patient's skin;

a laser; and a controller that receives signals generated by the at least one photosurface responsive to the imaged light and processes the signals to determine presence of localized contrasted regions on the skin and autonomously decides responsive to the determination whether the skin comprises a feature to be treated and where it is located;

wherein if such a feature is located, the controller autonomously controls the optics and laser to focus light from the laser for treating the feature, to a spot localized about the feature.

36. A laser system according to claim 35 wherein the photosurface comprises a quadrature detector.

37. A laser system according to claim 36 wherein signals from the quadrature detector are used to determine whether a contrasted sub-region imaged on the quadrature detector is substantially centered within the spot to which the laser light is focused.

* * * * *